United States Patent [19]

Mayer et al.

[11] 4,245,109
[45] Jan. 13, 1981

[54] PROCESS FOR PRODUCING ASTAXANTHIN

[75] Inventors: Hans J. Mayer, Füllinsdorf; Robert K. Müller, Basel, both of Switzerland

[73] Assignee: Hoffmann-La Roche Inc., Nutley, N.J.

[21] Appl. No.: 40,626

[22] Filed: May 21, 1979

[30] Foreign Application Priority Data

Jun. 2, 1978 [CH] Switzerland .......................... 6073/78
Mar. 29, 1979 [CH] Switzerland .......................... 2921/79

[51] Int. Cl.$^3$ ............................................ C07C 69/612
[52] U.S. Cl. ................................ 560/61; 260/340.9 R; 560/120; 560/259; 568/377
[58] Field of Search .................... 260/586 R; 560/259, 560/120, 61

[56] References Cited

U.S. PATENT DOCUMENTS

| | | | |
|---|---|---|---|
| 2,382,313 | 8/1945 | Henke | 560/120 |
| 3,773,824 | 11/1973 | Strong | 560/61 |
| 3,839,421 | 10/1974 | Schwieter et al. | 560/259 |
| 4,098,827 | 7/78 | Rosenberger | |
| 4,156,090 | 5/1979 | Kienzle | 560/61 |

FOREIGN PATENT DOCUMENTS 49-109337 10/1974 Japan .................................. 260/586 R

*Primary Examiner*—Ethel G. Love
*Attorney, Agent, or Firm*—Jon S. Saxe; George M. Gould; William H. Epstein

[57] ABSTRACT

The compound 5[4(acyloxy or protected hydroxy-3-oxo-2,6,6-trimethyl-cyclohex-1-en-1-yl)-3-methyl-penta-1,4-dien-3-ol], an intermediate for the coloring agent astaxanthin, its conversion to astaxanthin and its preparation from 4-oxo-$\beta$-ionone including intermediates in this synthesis.

6 Claims, No Drawings

PROCESS FOR PRODUCING ASTAXANTHIN

SUMMARY OF THE INVENTION

In accordance with this invention, it has been discovered that compounds of the formula

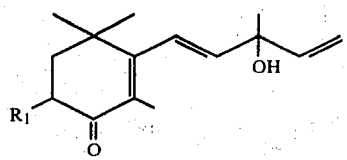
I wherein $R_1$ is acyloxy or an ether group convertable into hydroxy can be converted into the natural coloring agent astaxanthin.

The compound of formular I hereinbefore and formulae II, III and IV hereinafter include not only racemic compounds but also optically active compounds.

Racemic compounds of formula I have the general formula

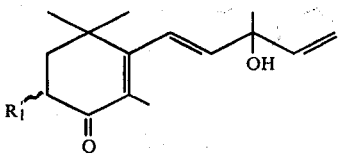
IAB optically active (S)-compounds of formula I have the general formula

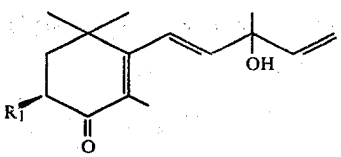
IA and optically active (R)-compounds of formula I have the general formula

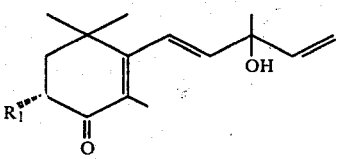
IB wherein $R_1$ is as above.

DETAILED DESCRIPTION OF THE INVENTION

The wavy line (~) denotes that the group $R_1$ can lie not only in front of but also behind the plane of the molecule. The wedge (▬) denotes that the group $R_1$ associated therewith lies in front of the plane of the molecule and the broken line (||||) denotes that the group $R_1$ attached thereto lies behind the plane of the molecule.

An acyloxy group $R_1$ can be derived, for example, from a lower or higher alkanecarboxylic acid or alkenecarboxylic acid as well as an aryl lower alkyl carboxylic acid. The lower members contain from 1 to 6 carbon atoms and the higer members contain from 7 to 20 carbon atoms. The lower and higher members are preferably substituted by halogen, alkoxy or aryloxy, because acyloxy groups substituted by halogen, alkoxy or aryloxy can be saponified to the hydroxy group in the present system without being partially transformed into the oxo group during the saponification. The acyloxy group can also be derived from an optically active acid usable as the resolving agent, for example (−)-camphanic acid.

Examples of acyloxy groups $R_1$ convertible into the hydroxy group are, of the lower members, the acetoxy, propionyloxy, butyryloxy, valeryloxy, pivaloyloxy and capryloxy groups as well as the monochloroacetoxy, dichloroacetoxy, ethoxyacetoxy and phenoxyacetoxy groups, and of the higher members, the palmitoyloxy, stearoyloxy and oleoyloxy groups. Of these groups the α-chloroacetoxy, α-ethoxyacetoxy and α-phenoxyacetoxy groups are preferred. $R_1$ can also be the (−)-camphanoloxy group.

As ether groups covertible into the hydroxy group there come into consideration ether groups which can readily be converted into the hydroxy group by hydrolysis, for example the 1-methoxy-1-methyl-ethoxy group or the tert. butoxy group.

As used herein the term aryl designates mononuclear or polynuclear aromatic hydrocarbon groups which can be unsubstituted or substituted in one or more positions with a lower alkyl radical such as phenyl, napthyl, anthryl, azulyl, tolyl, etc. The term alkyl designates saturated aliphatic straight or branched chain hydrocarbon groups containing from 1 to 6 carbon atoms such as methyl, ethyl, n-propyl, isopropyl, n-butyl, etc. The term alkylene oxide designates alkylene oxide containing from 2 to 20 carbon atoms, preferably 2 to 7 carbon atoms and having a single oxygen bridge. Among the preferred alkylene oxides are ethylene oxide, 1,2-butylene oxide and 1,2-propylene oxide. The term halogen as used herein includes all four halogens, i.e. chlorine, fluorine, bromine or iodine.

The process for the manufacture of the compounds of formula I comprises subjecting a racemic or optically active polyene compound of the general formula

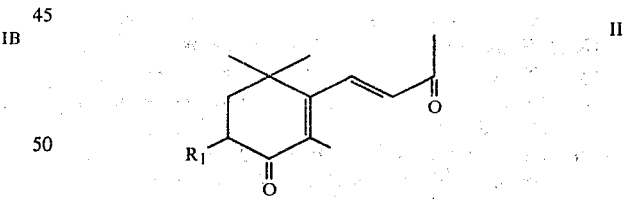
II wherein $R_1$ is as above, to vinylation or to ethynylation followed by partially hydrogenation.

It was to be expected that in the aforementioned process there would be obtained a mixture of products consisting of compounds vinylated or ethynylated on the side-chain and/or on the ring. It was also to be feared that the group $R_1$ would react with the vinylating or ethynylating agent. In both cases it is, however, surprisingly not the case.

Thus, if a vinylmagnesium halide or an ethynylmagnesium halide is allowed to act on a starting material of formula II dissolved in an aprotic solvent at a temperature below 0° C., then there is obtained almost exclusively the desired compound of formula I lengthened in the side-chain.

In carrying out this reaction, any conventional aprotic solvent can be used. Especially suitable aprotic solvents for use in the present process are tetrahydrofuran, diethyleneglycol dimethyl ether and ethyleneglycol dimethyl ether.

Any conditions conventional in ethynylation or vinylation can be used in carrying out these reactions. The preferred temperature range for the vinylation lies bettween about −30° C. and about 100° C. The preferred temperature range for the ethynylation lies between about −30° C. and +30° C.

In carrying out these reaction, any conventional ethynylating or vinylating agent can be utilized.

The preferred vinylating agents are vinylmagnesium chloride and bromide and the preferred ethynylating agents are ethynylmagnesium chloride and bromide.

The compounds of the general formula

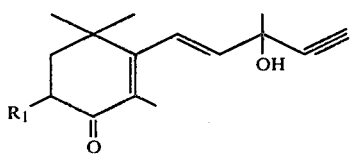   III wherein $R_1$ is as above initially obtained by the ethynylation of a compound of formula II are converted by partial hydrogenation into the desired compounds of formula I.

The partial hydrogenation of the ethynyl group to the vinyl group can be carried out in a manner known per se using a partially deactivated palladium catalyst (Lindlar catalyst) in a solvent such as benzene, toluene, ethyl acetate or an alkanol such as methanol or isopropanol and conveniently at normal pressure and room temperature.

The novel compounds of formula I hereinbefore are key compounds for the manufacture of racemic and optically active astaxanthin. 3(S),3′(S)-astaxanthin and 3(R),3′(R)-astaxanthin are natural products. They can be manufactured from the compounds of formulae IA or IB in the manner described hereinafter. Moreover, the meso form of the optically active astaxanthin, 3(R),3′(S)-astaxanthin, can also be obtained from the key compounds of formulae IA and IB. Astaxanthin is a red coloring substance which is in demand for the coloring of foodstuffs. Astaxanthin is widely distributed in nature, but can be isolated from natural sources only with considerable expense and in an unsatisfactory yield, not lastly because of the low concentration.

The starting materials of formula II can be prepared, for example, as follows:

The racemic starting materials of formula IIAB are prepared from 4-oxoionone (VI) via the following steps:

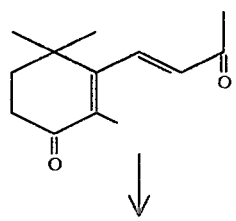   VI

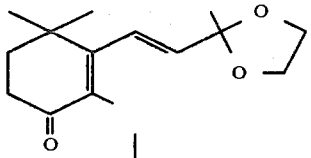   VII

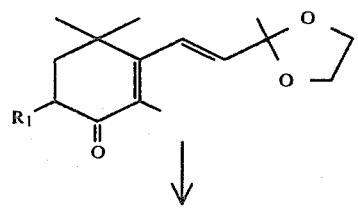   VIII

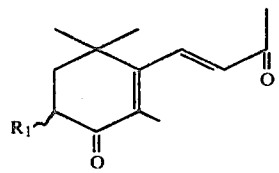   IIAB ($R_1$=acyloxy).

The optically active starting materials of formulae IIA and IIB in which $R_1$ represents an acyloxy group convertible into the hydroxy group can be prepared from the racemic starting materials of formula IIAB via the following steps:

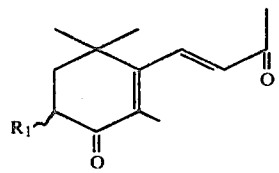   IIAB

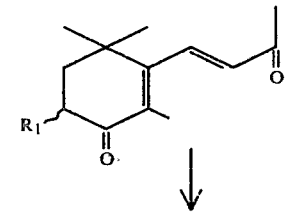   IXAB

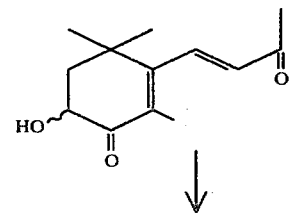   XAB

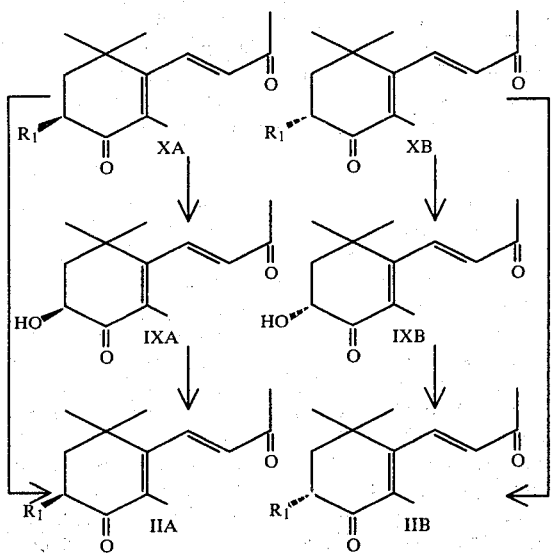

[R'₁ = acyloxy group derived from an acid suitable for racemate resolution, for example, (—)-camphanic acid].

The steps illustrated previously can be carried out as follows:

Preparation of a racemic 3-acyloxy-4-oxo-β-ionone (IIAB) from 4-oxo-β-ionone (VI):

4-Oxo-β-ionone (VI) is reacted in the presence of paratoluenesulphonic acid with 1.2 mol equivalents of ethyl orthoformate to give 4-oxo-β-ionone 9-ethylene ketal (VII). This ketal (VII) is converted by treatment with an acylating agent (e.g. lead tetraacetate) in a solvent (e.g. toluene) at the boiling point into a racemic 3-acyloxy-4-oxo-β-ionone 9-ethylene ketal (VIII) which is subsequently deketalised to give the desired racemic 3-acyloxy-4-oxo-β-ionone (IIAB) by shaking with water/methanol/glacial acetic acid (10:10:1) at room temperature.

Preparation of a 3-(S)-acyloxy-4-oxo-β-ionone (IIA) from a racemic 3-acyloxy-4-oxo-β-ionone (IIAB):

A racemic 3-acyloxy-4-oxo-β-ionone (IIAB) is saponified in an alkanol with the exclusion of oxygen using aqueous alkali, especially 1-N sodium hydroxide, to give racemic 3-hydroxy-4-oxo-β-ionone (IXAB). This alcohol (IXAB) is subsequently separated into its enantiomers. In order to be able to carry out this separation, the alcohol is esterified with a suitable acid, preferably (—)-camphanic acid. The esterification with (—)-camphanic acid chloride in pyridine yields a crystalline ester mixture (XAB) from which, for example by fractional crystallisation from ethyl acetate/hexane, the desired 3(S)-(—)-camphanoyloxy-4-oxo-β-ionone (XA) as well as 3(R)-(—)-camphanoyloxy-4-oxo-β-ionone (XB) can be isolated in high purity. The diastereomers (XA) and (XB) are examples of starting materials of formulae IIA and IIB in which R₁ represents the (—)-camphanoloxy group. The camphanic acid derivatives XA and XB can therefore be used directly as the starting materials for the vinylation or ethynylation in accordance with the invention.

However, in order to recover immediately the resolving agent, i.e. the (—)-camphanic acid, the resulting compounds of formulae XA and XB can also be firstly saponified to give 3(S)-hydroxy-4-oxo-β-ionone (IXA) or 3(R)-hydroxy-4-oxo-β-ionone (IXB) and these alcohols can subsequently be esterified by introducing one of the acyl groups mentioned hereinbefore to give a 3(S)-acyloxy-4-oxo-β-ionone (IIA) or a 3(R)-acyloxy-4-oxo-β-ionone (IIB).

The starting materials of formula II in which R₁ represents an ether group convertible into the hydroxy group can readily be prepared by etherifying 3-hydroxy-4-oxo-β-ionone.

As mentioned hereinbefore, the novel compounds of formula I are key compounds for the manufacture of racemic and optically active astaxanthin.

For the manufacture of astaxanthin, the compounds of formula I are transformed either by isomerization and oxidation or by halogenation and reaction with a triarylphosphine into a racemic or optically active $C_{15}$-building brick of the general formula

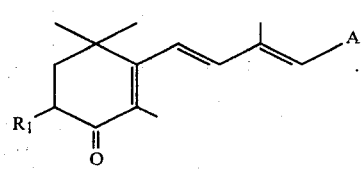

wherein $R_1$ is as above; A is formyl, halogen methyl (—CH₂ halogen) or a triarylphosphoniummethyl group of the formula —CH₂-P[X]₃⊕ Y⊖;X is aryl; and Y is an anion of an inorganic or organic acid, which is subsequently condensed with a $C_{10}$-building brick of the general formula

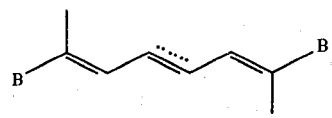

wherein B is a triarylphosphoniummethyl group of the formula —CH₂-P[X]₃⊕ Y⊖;X and Y are as above, or the formyl group, and the broken line denotes an optional carbon-carbon bond, to give a racemic or optically active astaxanthin or 15,15'-didehydroastaxanthin, protected in positions 3 and 3' by an acyl or ether group, or to give astaxanthin or 15,15'-didehydro-astaxanthin directly.

Acylates obtained can be converted into racemic and optically active astaxanthin by saponification and, where required, by partial hydrogenation.

Typical anions Y in the compounds of formula IV above are halogen ions, particularly the chloro and bromo ions, and the p-toluenesulphonate ion.

The compounds of formulae IV, where A is other than halogenmethyl, and V are condensed with one another under the conditions of a Wittig reaction in the presence of an acidbinding agent (e.g. an alkali metal alcoholate such as sodium methylate, lithium carbonate or sodium bicarbonate or an optionally alkyl-substituted alkylene oxide, especially ethylene oxide or 1,2-butylene oxide), if desired in a solvent (e.g. an alkanol such as isopropanol, a halogenated hydrocarbon such as methylene chloride or dimethylformamide). Any of the conditions conventional in carrying out Wittig reactions can be utilized in carrying out this reaction.

If the foregoing Wittig reactin used for the linkage of the condensation components of formulae IV, where A is other than halogenmethyl, and V is carried out in the presence of a protic solvent, then a hydrolytically readily removable acyl group present is split off under the condensation conditions and there is obtained directly racemic or optically active astaxanthin or 15,15′-didehydro-astaxanthin.

If, on the other hand, the condensation under the conditions of a Wittig reaction is carried out in an aprotic solvet (e.g. in diethyl ether), then even readily hydrolyzable acyl groups remain intact.

The term "protic solvent" as used above comprises particularly such protic solvents as alcohols, particularly lower aliphatic alcohols, such as methanol, ethanol and isopropanol.

The term "aprotic solvents" as used above comprises particularly such aprotic solvents as hydrocarbons, which may be halogenated, such as toluene, or methylene chloride.

The preferred acyloxy groups $R_1$ in compounds of formula IV are acyloxy groups substituted by chlorine or phenoxy. The tri(chloro or fluoro)acetoxy group, for example, has been shown to be less suitable because it is too labile, thereby reducing yields.

The hydrolytically removable acyl moieties of the acyloxy groups can be split off from the astaxanthin derivatives in a manner known per se. Because of the sensitivity of the molecule, the hydrolysis of the acyloxy groups is carried out under the most careful conditions possible. The acyloxy groups mentioned earlier can be readilysaponified to the hydroxy group by treatment with weak alkalis at a temperature between about −30° C. and about +50° C. The monochloroacetyl group and the dichloroacetyl group can be hydrolyzed by simply heating in water or in an aqueous alkanol.

The ether groups can be converted into the hydroxy group byhydrolysis. For example, the 1-methoxy-1-methyl-ethoxy group can be converted into the hydroxy group be treatment with aqueous hydrochloric acid and the tert. butoxy group can be converted into the hydroxy group by treatment with zinc chloride.

The following Examples further illustrate the present invention. Unless otherwise stated, temperatures are in degrees Celsius, and the ether is diethyl ether and the ratios are in parts by volume.

EXAMPLE 1

2.2 g of racemic 3-acetoxy-4-oxo-$\beta$-ionone are dissolved in 40 ml of absolute tetrahydrofuran. The solution is treated dropwise while stirring at about −75° C. under argon over a period of 30 minutes with 1:1 mol equivalents of a ca 1 molar solution of vinylmagnesium chloride in tetrahydrofuran. The cold solution is extracted with ether after the addition of 5 ml of a concentrated aqueous ammonium chloride solution. The ether extract is dried and evaporated under reduced pressure. The residual racemic 5[4-acetoxy-3-oxo-2,6,6-trimethyl-cyclohex-1-en-1-yl]-3-methyl-penta-1,4-dien-3-ol is purified by adsorption on silica gel using ether/hexane (4:1) for the elution. Colorless oil.

EXAMPLE 2

79.45 g of 4-oxo-$\beta$-ionone are introduced into 68.50 g of ethylorthoformate and, after the addition of 35.85 g of ethyleneglycol, the mixture is treated with 385 mg of paratoluenesulfonic acid while stirring. The mixture is stirred for 30 minutes and, after the addition of 1.93 g of sodium carbonate, for a further 5 minuts, then introduced into 250 ml of a concentrated aqueous sodium chloride solution, 250 ml of water and 500 g of ice and extracted with a total of 2000 ml of ether. The ether extract is washed with a half-concentrated aqueous sodium chloride solution and then with a concentrated aqueous sodium chloride solution, dried over sodium sulfate andd evaporated under reduced pressure. The residual 4-oxo-$\beta$-ionone 9-ethylene ketal melts at 35°–37° C. after recrystallization from pentane.

EXAMPLE 3

37.5 g of 4-oxo-$\beta$-ionone 9 ethylene ketal and 133.9 g of lead tetraacetate are heated to boiling for 8 hours under reflux after the addition of 600 ml of toluene. After cooling, the solution is filtered. For the deketalization, the 3-acetoxy-4-oxo-$\beta$-ionone 9-ethylene ketal remaining behind after evaporation of the filtrate is taken up in 525 ml of water/methanol/glacial acetic acid (10:10:1) and stirred for 12 hours, then introduced into 1000 ml of ice/water and extracted with a total of 1200 ml of ether. The ether extract is washed with a saturated aqueous sodium chloride solution with a saturated aqueous sodium hydrogen carbonate solution and again with a saturated aqueous sodium chloride solution, dried over sodium sulfate and evaporated under reduced pressure. The residual racemic 3acetoxy-4-oxo-$\beta$-ionone melts at 65°–67° C. after recrystallization from ether/hexane.

EXAMPLE 4

1.5 g of 3(S)-acetoxy-4-oxo-$\beta$-ionone are dissolved in25 ml of absolute tetrahydrofuran. The solution is treated dropwise while stirring at about −78° C. under argon over a period of 15 minutes with 6.3 ml of a 0.95 molar solution of vinylmagnesium chloride in tetrahydrofuran. The cold solution is stirred for 30 minutes, then introduced into 50 g of ice/water and, after the addition of 50 ml of a concentrated aqueous ammonium chloride solution, extracted with a total of 300 ml of ether. The ether extract is washed with two 100 ml portions of a semi-saturated aqueous sodium chloride solution, dried over sodium sulfate and evaporated under reduced pressure. The residual 5-[4(S)-acetoxy-3-oxo-2,6,6-trimethyl-cyclohex-1-en-1-yl]-3-methyl-penta-1,4-dien-3-ol is purified by adsorption on silica gel using ether/hexane (4:1) for the elution. Colorless viscous oil; $n_D^{24} = 1.4978$.

EXAMPLE 5

21.1 g of racemic 3acetoxy-4-oxo-$\beta$-ionone are dissolved in 80 ml of methanol. The solution is treated dropwise under argon at −5° C. over a period of 30 minutes with 80 ml of 1-N sodium hydroxide. The mixture is introduced into ice/water and extracted with ether. The ether extracct is washed, dried and subsequently evaporated under reduced pressure. The residual racemic 3hydroxy-4-oxo-$\beta$-ionone melts at 49.5°–51° C. after recrystallization from ether/hexane.

EXAMPLE 6

8.88 g of racemic 3hydroxy-4-oxo-$\beta$-ionone are dissolved in 40 ml of pyridine. The solution is treated while excluding moisture at 0° C. with 10.4 g of (−)-camphanic acid chloride. The mixture is stirred at 0° C. for 30 minutes and then at +15° C. for 3 hours, introduced into ice/water and extracted with chloroform. Pyridine residues still present are bound by the addition of dilute hydrochloric acid at 0° C. The mixture of the two diastereomeric (−)-camphanic acid esters, a viscous oil, remaining behind after evaporation of the solvent is separated up into the diastereomers as described hereinafter.

EXAMPLE 7

The diastereomer mixture of Example 6 is separated by chromatography on silica gel using ether/hexane (4:1) for the elution or by fractional crystallization from ethyl acetate/hexane into 3(S)-(−)-camphanoyloxy-4-oxo-β-ionone (melting point 119°–120° C.) and 3(R)-(−)-camphanoyloxy-4-oxo-β-ionone (melting point 124°–126° C.).

EXAMPLE 8

2.01 g 3(S)-(−)-camphanoyloxy-4-oxo-β-ionone are treated dropwise, after the addition of 30 ml of absolute methanol, while extruding oxygen and stirring at 0° C. over a period of 15 minutes with 5.2 ml of 1-N sodium hydroxide. The mixture is stirred at room temperature for 3 hours, then introduced into 100 g of ice/water and, after the addition of 100 ml of concentrated aqueous sodium chloride solution, extracted with 300 ml of ether. The ether extract is washed with two 100 ml portions of a half-concentrated aqueous sodium chloride solution, dried over sodium sulfate and evaporated under reduced pressure. The residual 3(S)-hydroxy-4-oxo-β-ionone melts at 36°–37° C. after purification by adsorption on silica gel using ether/hexane (4:1) for the elution and crystallization from ether/hexane; $[\alpha]_n = -97.2°$ (ethanol).

The saponification of 3(R)-(−)-camphanoyloxy-4-oxo-β-ionone in an analogusmanner yields 3(R)-hydroxy-4-oxo-β-ionone of melting point 35°–36° C.

EXAMPLE 9

160 mg of 3(S)-hydroxy-4-oxo-β-ionone are dissolved in 1.6 ml of pyridine. After the addition of 0.4 ml of acetic acid anhydride, the solution is stirred at room temperature for 16 hours. The mixtue is then introduced into 20 g of ice/water and extracted three times with 30 ml of ether each time. The combined ether extracts are, with the addition of ice, washed twice with 20 ml portions of half-concentrated aqueous sodium chloride solution, twice with 20 ml portions of 1-N hydrochloric acid and once with 20 ml of a half-concentrated aqueous sodium chloride solution, dried over sodium sulfate and evaporated under reduced pressure. The residual 2(S)-acetoxy-4-oxo-β-ionone melts at 64°–66° C. after recrystallization from ether/hexane; $[\alpha]_n = 97.3°$ (ethanol).

EXAMPLE 10

4.02 g of 3(R)-(−)-camphanoyloxy-4-oxo-β-ionone are dissolved in 70 ml of tetrahydrofuran. The solution is treated dropwise at −75° C. under argon over a period of 10 minutes with 11 ml of a 0.95 molar solution of vinylmagnesium chloride in tetrahydrofuran. The cold mixture is introduced into ice/concentrated ammonium chloride and extracted with ether. The ether extract is washed, dried and then evaporated under reduced pressure. The residual, initially oily, 5-[4(R)-(−)-camphanoyloxy-3-oxo-2,6,6-trimethyl-cyclohex-1-en-1-yl]-3-methyl-penta-1,4-dien3-ol melts at 124°–126° C. after purification by adsorption on silica gel and crystallization from ether/hexane.

EXAMPLE 11

A solution of ethynylmagnesium bromide, prepared from 0.48 g of magnesium, 2.40 g of ethyl bromide and gaseous acetylene, in 60 ml of tetrahydrofuran is treated dropwise at 0° C. under argon with a solution of 2.64 g of 3-acetoxy-4-oxo-β-ionone in 10 ml of tetrahydrofuran. After 25 minutes, the mixture is introduced into an ice-cold saturated aqueous ammonium chloride solution and extracted with ether. The ether extract is washed neutral with a saturated aqueous sodium chloride solution, dried over sodium sulfate and evaporated under reduced pressure. The residual 3-acetoxy-4-oxo-ethynyl-β-ionol is purified by adsorption on silica gel using methylene chloride/ether (9:1) for the elution and is processed further as follows:

0.81 g of 3-acetoxy-4-oxo-ethynyl-β-ionol is dissolved in 15 ml of methanol. The solution is treated with 1.4 ml of 0.75% by weight solution of dimethylethanolamine in n-hexane and with 1.4 ml of a 0.0125% by weight solution of 1,2-bis-(2-hydroxy-ethylthio)-ethanol in ether. After the addition of 25 mg of Lindlar catalyst, the mixture is hydrogenated at normal pressure and room temperature. The solution, separated from the catalyst, is subsequently evaporated under reduced pressure. The residual 3-acetoxy-4-oxo-vinyl-β-ionol [racemic 5-[4-acetoxy-3-oxo-2,6,6-trimethyl-cyclohex-1-en-1-yl]-3methyl-penta-1,4-dien-3-ol] is a colorless oil; $n_D^{24} = 1.4978$.

EXAMPLE 12

Manufacture of racemic astaxanthin from racemic 5-[4-phenoxyacetoxy)-3-oxo-2,6,6-trimethyl-cyclohex-1-en-1-yl]-3-methyl-penta-2,4-diene-1-triphenylphosphonium bromide (IVAB) and 2,7-dimethyl-octa-2,4,6-triene-1,8dial.

4.4 g of racemic 5[4-(phenoxyacetoxy)-3-oxo-2,6,6-trimethyl-cyclohex-1-en-1-yl]-3-methyl-penta-2,4-diene-1-triphenylphosphonium bromide and 0.3 g of 2,7-dimethyl-octa-2,4,6-triene-1,8-dial are dissolved in 70 ml of isopropanol. After the addition of 3.5 ml of 2-N sodium methylate, the solution is stirred at room temperature for 1 hour, then introduced into water and extracted with methylene chloride. The racemic astaxanthin remaining behind after evaporation of the extract melts at 216°–218° C. after recrystallization from chloroform/methanol or pyridine/water.

EXAMPLE 13

4.5 g of racemic 5-[4-(phenoxyacetoxy)-3-oxo-2,6,6-trimethyl-cyclohex-1-en-1-yl]-3-methyl-penta-1,4-dien-3-ol are dissolved in 100 ml of diethyl ether. After the addition of 2ml of pyridine, the solution is treated dropwise at 0° C. with 1.2 g of phosphorus tribromide. The mixture is stirred for 2 hours, then introduced into water and extracteed with diethyl ether. The ether extract is evaporated. The residual bromide is taken up in ethyl acetate and treated with 2.9 g of triphenylphosphine. The racemic 2(E),4(E)-5-[4-phenoxyacetyl-3-oxo-2,6,6-tirmethyl-cyclohex-1-en-1-yl]-3-methyl-penta-2,4-diene-1-triphenylphosphonium bromide which crystallizes out in the course of 24 hours melts at 158°–161° C.

EXAMPLE 14

Manufacture of 3(S),3'(S)-astaxanthin from 5-[4-(S)-chloroacetoxy)-3-oxo-2,6,6-trimethyl-cyclohex-1en-1-yl]-3-methyl-penta-2,4-dien-1-al and 2,7-dimethyl-octa-2,4,6-triene-1,8-bis-triphenylphosphonium bromide:

0.01 mol of butyl lithium in 300 ml of diethyl ether/-hexane (3:1) is treated at −30° C. while stirring vigorously with 0.05 ml of 2,7-dimethyl-octa-2,4,6-triene-1,8- bis-triphenylphosphonium bromide. After 10 minutes, there are added dropwise 0.008 mol of 5-[4(S)-(chloroacetoxy)-3-oxo-2,6,6-trimethyl-cyclohex-1-en-1-yl]-3-methyl-penta-2,4-dien-1-al in 100 ml of diethyl ether. The mixture is stirred for 8 hours and subsequently evaporated. The residual 3(S),3'(S)-astaxantin dichloroacetate is taken up in methanol and heated to boiling under reflux. The solution obtained is purified by adsorption on silica gel. The pure 3(S),3'(S)-astaxanthin melts at 215°–217° C.

EXAMPLE 15

47.8 g of 5-[4(S)-(chloroacetoxy)-3-oxo-2,6,6-trimethyl-cyclohex-1-en-1-yl]-3-methyl-penta-1,4-dien-3-ol are dissolved in 720 ml of methylene chloride. After the addition of 200 ml of formic acid, the solution is stirred at room temperture for 45 minutes, then introduced into water and extracted with diethyl ether. The ether extract is evaporated. The residue is taken up in 500 ml of methanol, treated with 100 g of potassium carbonate 250 ml of water, stirred for 1 hour, then introduced into water and extracted with ethyl acetate. The 5-[4(S)-(chloroacetoxy)-3-oxo-2,6,6-trimethyl-cyclohex-1-en-1-yl]-3-methyl-penta-2,4-dien-1-ol isolated from the extract is processed further as follows:

29.7 g of 5-[4(S)-(chloroacetoxy)-3-oxo-2,6,6-trimethyl-cyclohex-1-en-1-yl]-3-methyl-penta-2,4-dien-1-ol are dissolved in 3000 ml of methylene chloride. After the addition of 1000 g of manganese dioxide, the solution is stirred for 45 minutes and then filtered. After evaporation of filtrate, 5-[4-(S)-(chloroacetoxy)-3-oxo-2,6,6-trimethyl-cyclohex-1-en-1-yl]-3-methyl-penta-2,4-dien-1-al remains behind.

EXAMPLE 16

Manufacture of 3(R),3'(R)-astaxanthin from 5-[4(R)-(−)-camphanoyloxy-3-oxo-2,6,6-trimethyl-cyclohex-1-en-1-yl]-3-methyl-penta-2,4-diene-1-triphenylphosphonium bromide (IVB) and 2,7-dimethyl-octa-2,4,6-triene-1,8-dial.

3.6 g of 5-[4(R)-(—)-camphanoyloxy-3-oxo-2,6,6-trimethyl-cyclohex-1-en-1-yl]-3-methyl-penta-2,4-diene-1-triphenylphosphonium bromide are dissolved in 60 ml of absolute isopropanol under argon. After the addition of 300 mg of 2,7-dimethyl-octa-2,4,6-triene-1,8-dial, the solution is stirred at room temperature for 30 minutes and then treated dropwise over a period of 10 minutes with 2.4 ml of solution of 2-N sodium methylate in methanol. The mixture is stirred at room temperature for 30 minutes and then at 0° C. for 1 hour, and subsequently filtered under an inert gas. The 3(R),3'(R)-astaxathin remaining behind on the filter melts at 216°–219° C. after purification by adsorption on silica gel using methylene chloride/ether/methanol (89:10:1) for the elution and crystallization from methylene chloride/methanol.

EXAMPLE 17

2.8 g of 5-[4(R)-(—)-camphanoyloxy-3-oxo-2,6,6-trimethyl-cyclohex-1-en 1-yl]-3-methyl-penta-1,4-dien-3-ol are dissolved in 30 ml of methylene chloride. After the addition of 2.28 g of triphenylphosphine hydrobromide, the solution is stirred at room temperature for 3 hours under argon. The solution is concentrated and treated with ethyl acetate. The separated crude 5-[4(R)-(−)-camphanoyloxy-3-oxo-2,6,6-trimethyl-cyclohex-1-en-1-yl]-3-methyl-penta-2,4-diene-1-triphenylphosphonium bromide is processed further as described in Example 16 without further purification.

EXAMPLE 18

22.2 g of racemic 3-hydroxy-4-oxo-β-ionone are dissolved in 210 ml of isopropenyl methyl ether and the solution is cooled to 0° C. 1 mg of paratoluenesulfonic acid is added to the solution while stirring, the ice-bath is removed and the mixture is stirred for a further 30 minutes while simultaneously warming to room temperature. There are now added 5 drops of triethylamine and 50 ml of methylene chloride, and the mixture is evaporated under reduced pressure. Crystallization of the residue from a small amount of methylene chloride/hexane yields 26.9 g of colorless racemic 6-(1-methoxy-1-methylethoxy)-2,4,4-trimethyl-3-(3-oxo-1-butenyl)-2-cyclohexen-1-one of melting point 107°–109° C.

14.72 g of racemic 6-(1-methoxy-1-methylethoxy)-2,4,4-trimethyl-3-(3-oxo-1-butenyl)-2-cyclohexen-1-one are dissolved in 200 ml of absolute tetrahydrofuran and the solution is cooled to about −70° C., a part of the educt again separating out. 35 ml of a 16.9% by weight vinylmagnesium chloride solution in tetrahydrofuran are now added dropwise while stirring over a period of 45 minutes. The mixture is left to warm to −45° C. over a period of about 30 minutes, the mixture becoming homogeneous. The mixture is then extracted with ether, the ether is evaporated and the residue is taken up in hexane. Crystallization at about −15° C. gives 3-(3-hydroxy-3-methyl-1,4-pentadienyl)-6-(1-methoxy-1-methylethoxy)-2,4,4-trimethyl-2-cyclohexen-1-one of melting point 64°–67° C.

The mixture obtained in the foregoing reaction is poured into a mixture of 150 ml of 1-N aqueous hydrochloric acid and 300 ml of half-concentracted sodium chloride solution, the resulting mixture is stirred for 30 minutes and then extracted with ether. The initially oily 6-hydroxy-3-(3-hydroxy-3-methyl-1,4-pentadienyl)-2,4,4-trimethyl-2-cyclohexen-1-one which remains behind after removal of the solvent is purified by adsorption of silica gel using ether/hexane for the elution. Colorless crystals of melting point 47.5°–49° C. can be crystallized very slowly at 0° C. from ether/hexane.

To a solution, cooled in an ice-bath, of 5.9 g of oily 6-hydroxy-3-(3-hydroxy-3-methyl-1,4-pentadienyl)-2,4,4-trimethyl-2-cyclohexen-1-one in 40 ml of methylene chloride are added 7.14 ml of 63% by weight hydrobromic acid in such a manner that the temperature remains below 5° C. 200 ml of ethyl acetate are added thereto and the organic phase is washed once with 100 ml of half-concentrated sodium chloride solution and twice with 100 ml of portions of half-concentrated sodium bicarbonate solution, 0.2 ml of butylene oxide is added thereto and the bromide solution is concentrated to 120 ml at 2° C. (bath temperature) in a water-jet vacuum. It is added dropwise while stirring to a solution of 6.18 g of triphenylphosphine in 40 ml of ethyl acetate and 0.2 ml of butylene oxide, the mixture is stirred for 15 hours at room temperature and then filtered. There are obtained 10.2 g of racemic 5-[4-hydroxy-3-oxo-2,6,6-trimethyl-cyclohex-1-en-1-yl]-3-methylpenta-2,4-diene-1-triphenylphosphonium bromide (melting point 172°–175° C.), (after recrystallization from a mixture of 50 ml of methylene chloride and 100 ml of ethyl acetate at 0° C. 8.8 g of melting point 178°–180° C.), which is converted into racemic astaxanthin by reaction with 2,7-dimethyl-octa-2,4,6-triene-1,8-dial.

We claim:

1. A compound of the formula

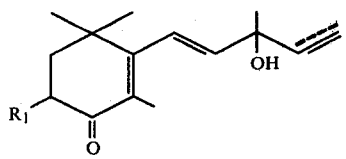

wherein $R_1$ is acyloxy or an ether group convertible into a hydroxy group; and the dotted bond can be optionally hydrogenated.

2. The compound of claim 1 wherein said compound is 5-[4-acetoxy-3-oxo-2,6,6-trimethyl-cyclohex-1-en-1-yl]-3-methyl-penta-1,4-dien-3-ol.

3. The compound of claim 1 wherein said compound is 3-acetoxy-4-oxo-ethynyl-β-ionol.

4. The compound of claim 1 wherein said compound is 5[4-(phenoxyacetoxy)-3-oxo-2,6,6-trimethyl-cyclohex-1-en-1-yl]-3-methyl-penta-1,4-dien-3-ol.

5. The compound of claim 1 wherein said compound is 3-(3-hydroxy-3-methyl-1,4-pentadienyl)-6-(1-methoxy-1-methylethoxy)-2,4,4-trimethyl-2-cyclohex-1-one.

6. The compound of claim 1 wherein said compound is 5-[4(R)-(−)-camphanoyloxy-3-oxo-2,6,6-trimethyl-cyclohexen-1-en-1-yl]-3-methyl-penta-1,4-dien-3-ol.

* * * * *